United States Patent
Herlihy et al.

(10) Patent No.: US 7,335,782 B2
(45) Date of Patent: Feb. 26, 2008

(54) THIOXANTHONE DERIVATIVES, AND THEIR USE AS CATIONIC PHOTOINITIATORS

(75) Inventors: Shaun L. Herlihy, Chatham (GB); Robert S. Davidson, Leicester (GB)

(73) Assignee: Sun Chemical Co., Parsippany, NJ (US)

( * ) Notice: Subject to any disclaimer, the term of this patent is extended or adjusted under 35 U.S.C. 154(b) by 524 days.

(21) Appl. No.: 10/505,615

(22) PCT Filed: Feb. 26, 2003

(86) PCT No.: PCT/US03/05820

§ 371 (c)(1),
(2), (4) Date: Mar. 16, 2005

(87) PCT Pub. No.: WO03/072568

PCT Pub. Date: Sep. 4, 2003

(65) Prior Publication Data

US 2005/0165126 A1    Jul. 28, 2005

(30) Foreign Application Priority Data

Feb. 26, 2002   (GB) .................................. 0204468.3

(51) Int. Cl.
     *C07D 335/08*    (2006.01)
(52) U.S. Cl. ..................................... 549/27
(58) Field of Classification Search .................. 549/27
     See application file for complete search history.

(56) References Cited

U.S. PATENT DOCUMENTS

| | | | |
|---|---|---|---|
| 4,694,029 A | | 9/1987 | Land .............................. 522/8 |
| 5,414,092 A | * | 5/1995 | Green et al. .................. 549/27 |
| 6,025,408 A | * | 2/2000 | Williams et al. ............... 522/53 |
| 6,960,668 B2 | * | 11/2005 | Timms et al. ................. 549/27 |
| 7,126,011 B2 | * | 10/2006 | Berg ............................ 549/27 |

\* cited by examiner

Primary Examiner—Deborah C. Lambkin
(74) Attorney, Agent, or Firm—Dickstein, Shapiro, LLP.

(57) ABSTRACT

Photoinitiator compounds of formula (I):

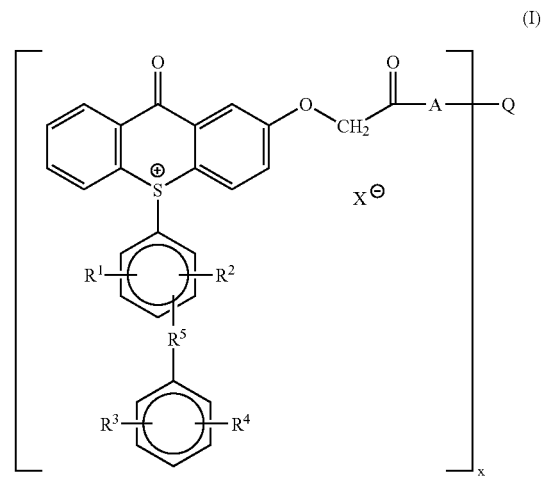

{where: A represents a direct bond or a group of formula $-[O(CHR^7CHR^6)_a]_y-$, $-[O(CH_2)_bCO]_y-$, or $-[O(CH_2)_bCO]_{(y-1)}-[O(CHR^7CHR^6)_a]-$, where one of $R^6$ and $R^7$ is hydrogen and the other is hydrogen or methyl; a is a number from 1 to 2; b is a number from 4 to 5; Q is a residue of a polyhydroxy compound having 2 to 6 hydroxy groups; x is a number greater than 1 but no greater than the number of available hydroxyl groups in Q; y is a number from 1 to 10; $R^1$, $R^2$, $R^3$ and $R^4$ are individually the same or different and each is hydrogen, hydroxy, or alkyl; or $R^1$ and $R^3$ are joined to form a fused ring system with the benzene rings to which they are attached; and $R^5$ represents a direct bond, an oxygen atom or a methylene group} are useful as cationic photoinitiators, especially for use in surface coating applications, such as printing inks and varnishes, and which are intended to be cured by polymerisation initiated by radiation.

22 Claims, No Drawings

THIOXANTHONE DERIVATIVES, AND THEIR USE AS CATIONIC PHOTOINITIATORS

The present invention relates to a series of novel thioxanthone derivatives which are useful as cationic photoinitiators, especially for use in surface coating applications, such as printing inks and varnishes, and which are intended to be cured by polymerisation initiated by radiation.

Photocurable compositions are cured by exposure to radiation, usually ultraviolet radiation, and include for example, lacquers which may be applied to wood, metal or similar substrates by suitable techniques such as roll coating or curtain coating. They may also be formulated as inks, for example to be applied by techniques such as letterpress, offset lithography, rotogravure printing, silk screen printing, inkjet or flexographic printing. Printing, depending on the particular printing technique, is applicable to a wide range of substrates which include paper, board, glass, plastics materials or metals. Other application areas will include adhesives powder coatings, circuit boards and microelectronic products, stereolithography, composites, optical fibres and liquid crystals.

Initiation of polymerisation in a monomer or prepolymer may be effected in a number of ways. One such way is by irradiation, for example with ultraviolet radiation, in which case it is normally necessary that the polymerisable composition should contain an initiator, commonly referred to as a "photoinitiator", or alternatively by an electron beam. There are two main types of curing chemistry which can be used in this process; free radical and cationic. Although cationic curing has many advantages, its disadvantages, particularly with regard to the photoinitiators used, leads it to be used only in a minority of applications. Most frequently used cationic initiators are either organic iodonium or sulphonium salts.

Briefly, the mechanism by which a sulphonium cationic initiator acts when irradiated is that it forms an excited state which then breaks down to release a radical caton. This radical cation reacts with the solvent, or another hydrogen atom donor, generating a protonic acid. The active species is the protonic acid. However, amongst the breakdown products of sulphonium salts are aromatic sulphides, such as diphenyl sulphide, which are malodorous and can be a health hazard, and lower aromatic hydrocarbons, such as benzene, which are potentially carcinogenic. Many of the commonly used iodonium salts break down to give volatile species such as benzene, toluene or isobutyl benzene. This places severe restrictions upon the applications for which such cationic photoinitiators can be used. For example, they cannot be used in printing inks on packaging intended for food or is likely to come into contact with food, and, in some cases, cannot be used at all where the packaging is to be handled by the consumer. Indeed, as the industry becomes ever more conscious of health matters, it is increasingly difficult to use such compounds at all and there is, therefore, an urgent need to find compounds suitable for use as photoinitiators and whose breakdown products are generally regarded as safe.

However, this, although important, is not the only constraint upon the choice of compound to be used as a cationic photoinitiator. Even without consideration of the health issues, the cleavage products of the known cationic photoinitiators are malodorous, and it is highly desirable that unpleasant odours should be minimised. This leads to a desire that the cleavage products should be relatively non-volatile and non-odorous. The cationic photoinitiators must, of course, also be sufficiently stable, both as isolated compounds and when in the uncured coating formulation. They must also be soluble in or miscible with other components of the uncured coating formulation. Finally, they should be able to absorb radiation over a suitable and sufficiently wide range of wave lengths, ideally without the use of a sensitiser.

What is more, the nature of the cationic photoinitiator can have a major impact on the properties of the cured coating. The cationic photoinitiator should produce a coating which is fully cured, hard and resistant to common solvents and abuse.

Finally, there are a number of practical problems associated with the manufacture of the compounds used as cationic photoinitiators, including the necessity that they should be relatively easy and inexpensive to manufacture.

Thus, it would be desirable to provide a cationic photoinitiator which does not generate malodorous or toxic by-products upon radiation cure, particularly diphenyl sulphide and benzene, and so which may be used for printing packaging which may come into contact with food. Moreover it is a common desideratum in this field that the photoinitiator should possess the following properties: good solubility, good cure performance, good adhesion to substrates and reasonable cost.

Not surprisingly, complying with all of these, often conflicting, requirements is not easy, and we are not aware of any completely satisfactory commercial solution available until now.

However, we have now discovered a series of new thioxanthone derivatives, whose breakdown products can be compounds which themselves are accepted as food ingredients and whose safety, therefore, cannot be questioned. Moreover, many of these compounds have the advantages of good solubility in the coating composition combined with excellent cure. These compounds have a biphenylyl or phenoxy- or benzyl-substituted phenyl group attached to the thioxanthone ring. Thus, the potential by-products of these new compounds would be thioxanthone derivatives typical of those used widely in free-radical curing inks for food packaging, and biphenyl, which is itself an approved anti-oxidant food additive in Europe, or diphenyl oxide or diphenylmethane, which are generally regarded as non-toxic in small quantities.

Thus, the present invention provides photoinitiator compounds of formula (I):

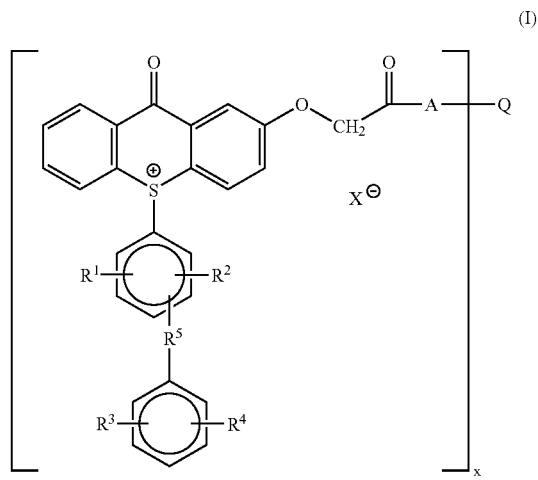

where:

A represents a direct bond or a group of formula —[O(CHR$^7$CHR$^6$)$_a$]$_y$—, —[O(CH$_2$)$_b$CO]$_y$—, or —[O(CH$_2$)$_b$CO]$_{(y-1)}$—[O(CHR$^7$CHR$^6$)$_a$]—, where:

one of R$^6$ and R$^7$ represents a hydrogen atom and the other represents a hydrogen atom or a methyl group;

a is a number from 1 to 2;

b is a number from 4 to 5;

Q is a residue of a polyol having from 2 to 6 hydroxy groups;

x is a number greater than 1 but no greater than the number of available hydroxyl groups in Q;

when x is a number greater than 1 but no greater than 2, y is a number from 1 to 10;

or when x is a number greater than 2, y is a number from 3 to 10;

R$^1$, R$^2$, R$^3$ and R$^4$ are individually the same or different and each represents a hydrogen atom, a hydroxy group, or an alkyl group having from 1 to 4 carbon atoms;

or R$^1$ and R$^3$ are joined to form a fused ring system with the benzene rings to which they are attached;

and

R$^5$ represents a direct bond, an oxygen atom or a methylene group.

These compounds are useful as photoinitiators for use in energy, e.g. UV, curable coating compositions, including varnishes, lacquers and printing inks, most especially printing inks.

The compounds of the present invention may, as described above, be used as cationic photoinitiators for radiation-curable coating compositions. Thus, the present invention also provides a radiation-curable composition comprising: (a) a polymerisable monomer, prepolymer or oligomer, especially a material which undergoes acid-catalysed ring opening polymerisation, e.g. an epoxide (oxirane) or oxetane, or an ethylenically unsaturated material, such as vinyl or propenyl ethers and (b) a cationic photoinitiator which is a compound of formula (I), as defined above.

The invention still further provides a process for preparing a cured polymeric composition by exposing a composition of the present invention to curing energy, preferably ultraviolet radiation.

For the avoidance of doubt, the numbering system employed for the thioxanthone derivatives is as shown in the following formula:

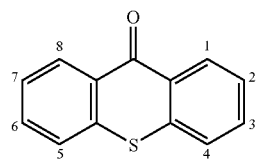

In the compounds of the present invention, we prefer that A should represent a group of formula —[O(CHR$^2$CHR$^1$)$_a$]$_y$— where a is an integer from 1 to 2, and y is as defined above, preferably a number from 1 to 10, more preferably a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is as defined above, preferably a number from 3 to 10, or a group of formula —[O(CH$_2$)$_b$CO]$_y$— or —[O(CH$_2$)$_b$CO]$_{(y-1)}$—[O(CHR$^2$CHR$^1$)$_a$]—, where b is a number from 4 to 5 and y is as defined above, preferably a number from 3 to 10. Still more preferably, y is a number from 3 to 6.

It is preferred, in accordance with the present invention, that the compounds are of a generally polymeric nature. The polymeric nature may be provided by either the group represented by Q or the group represented by A or by both.

The polyhydroxy residue of formula Q-(A-)$_x$, which may be polymeric and which forms the core of the compounds of the present invention has a major influence on the behaviour of the compounds. In accordance with the present invention, it is preferred that it should have a polymeric nature, since the resulting compounds tend to be liquid or of low melting point, thus aiding dispersion in the coating composition. Compounds having a similar structure but not polymeric tend to be solid and/or less soluble in these coating compositions. However, we prefer that the core residue, of formula Q-(A-)$_x$, should not have too high a molecular weight, and prefer that the residue of formula Q-(A-)$_x$ should have a molecular weight no greater than 2000, preferably no greater than 1200, still more preferably no greater than 1000, and most preferably no greater than 800.

We particularly prefer that Q should be a residue of ethylene glycol, propylene glycol, butylene glycol, glycerol, trimethylolpropane, di-trimethylolpropane, pentaerythritol or di-pentaerythritol.

Alternatively, A may represent a direct bond, in which case, the residue Q is attached directly to the carbonylmethoxy group at the 2-position of the thioxanthone ring system. In this case, Q is preferably a residue of an alkanediol. The nature of the alkanediol is not critical to the invention, although relatively longer chain compounds are preferred. However, in general, the alkanediol may be a straight or branched chain compound having from 2 to 30 carbon atoms, for example, ethylene glycol, propylene glycol, butylene glycol (preferably 1,3-, 1,4- or 2,3-), pentanediol, hexanediol, octanediol, nonanediol, decanediol, dodecanediol, tridecanediol, tetradecanediol, pentadecanediol, hexadecanediol, heptadecanediol, octadecanediol, nonadecanediol, icosanediol, henicosanediol, docosanediol, icosanediol or triacosanediol, of which hexanediol and decanediol are preferred.

It will be appreciated that, when the compounds of the present invention are analysed, the numbers a, b and y in the above formulae need not be integral, and, indeed, it is unlikely that they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

Where R$^1$, R$^2$, R$^3$ or R$^4$ represents an alkyl group, this may be a straight or branched chain alkyl group having from 1 to 4 carbon atoms, and examples include the methyl, ethyl propyl, isopropyl, butyl, isobutyl and t-butyl groups, of which the methyl group is preferred.

We prefer those compounds of formula (I) in which two, three or four of R$^1$, R$^2$, R$^3$ and R$^4$ represent hydrogen atoms, and especially those in which all of R$^1$, R$^2$, R$^3$ and R$^4$ represent hydrogen atoms.

When $R^2$ and $R^4$, together with the benzene rings to which they are attached, form a fused ring system, this may be, for example, a biphenylene, fluorene or phenanthrene system, preferably fluorene.

$R^5$ may be a direct bond (so that the two groups joined by $R^5$ together form a biphenylyl group), an oxygen atom (so that the two groups joined by $R^5$ together form a phenoxyphenyl group), or a methylene group (so that the two groups joined by $R^5$ together form a benzylphenyl group). Of these, the direct bond is preferred, since the breakdown product of the resulting compounds, biphenyl, is non-toxic.

$X^-$ represents an anion. In general, there is no particular limitation on the nature of the anion to be used. However, where the compounds of the present invention are to be used as photoinitiators, the anion should be non-nucleophilic, or essentially non-nucleophilic, as is well known in the art. It should also be relatively bulky. If the compounds are not to be used as photoinitiators, the anion need not meet these requirements. For example, in some cases, it may be desirable not to store the compound in the form of the salt which is ultimately to be used. In that case, it may be preferable to form another salt, and then convert the compound to the desired salt at or close to the point of use. In such a case, it is not necessary that the anion should be non-nucleophilic.

Examples of non-nucleophilic anions are well known to those skilled in the art, and include anions of formula $MZ_n^-$ where M represents a phosphorus, boron, antimony, arsenic, chlorine or carbon atom, Z represents a halogen atom except where M represents a halogen atom, an oxygen atom or a sulphite group, and n is an integer dependent upon the valence of M and Z. Preferred examples of such groups include the $PF_6^-$, $SbF_6^-$, $AsF_6^-$, $BF_4^-$, $B(C_6F_5)_4^-$, $R^aB(Ph)_3^-$ (where $R^a$ represents an alkyl group having from 1 to 6 carbon atoms and Ph represents a phenyl group), $R^bSO_3^-$ (where $R^b$ represents an alkyl or haloalkyl group having from 1 to 6 carbon atoms or an aryl group), $ClO_4^-$ and $ArSO_3^-$ (where Ar represents an aryl group) groups, of which the $PF_6^-$, $SbF_6^-$, $AsF_6$, $CF_3SO_3^-$ and $BF_4^-$ groups are preferred and the $PF_6^-$ group is most preferred.

The compounds of the present invention may be prepared by reactions well known for the preparation of compounds of this type, the exact reaction route chosen depending upon the nature of the compound which it is desired to prepare.

For example, the compounds may be prepared as follows.

In a first step, 2-carboxymethoxythioxanthone (II):

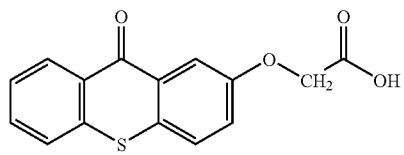

is reacted with a core compound of formula (III):

(where A, x and Q are as defined above), to give a compound of formula (IV):

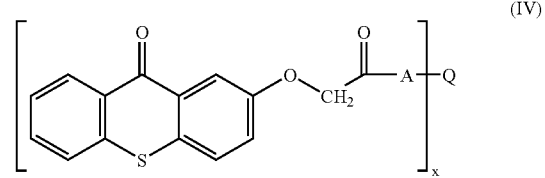

where A, x and Q are as defined above.

The reaction is normally and preferably effected in the presence of a solvent, the nature of which is not critical to the present invention, provided that it has no adverse effect on the reagents or on the reaction. Examples of suitable solvents include: aromatic hydrocarbons, such as benzene, toluene or xylene.

The reaction is preferably effected in the presence of an acidic catalyst, for example: a sulphonic acid, such as p-toluenesulphonic acid or methanesulphonic acid; a mineral acid, such as sulphuric, hydrochloric or phosphoric acid; or a Lewis acid, such as aluminium chloride, boron trifluoride or an organotitanate.

The temperature at which the reaction is carried out is likewise not critical to the present invention and may vary widely, depending on the reaction and the nature of the reagents and solvent, provided that it is sufficiently high that the water formed in the course of the reaction is removed, in order to drive the reaction to completion. We therefore generally find it convenient to carry out the reaction at about the reflux temperature of the reaction mixture. The time required for the reaction may also vary widely, depending mainly on the reaction temperature. However, under the preferred conditions outlined above, a period of from 1 to 20 hours will normally suffice.

When the reaction is complete, the desired product may be removed from the reaction mixture by conventional means, for example by washing the reaction mixture, e.g. with water and/or and aqueous alkali, drying and then removing the solvent by evaporation under reduced pressure.

The resulting compound of formula (IV) is then oxidised to give the corresponding sulphoxide of formula (V):

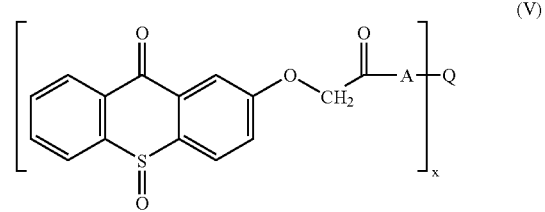

where A, x and Q are as defined above.

This reaction may be carried out by conventional means using any suitable oxidising agent known for use in this type of reaction. The oxidising agent used should be capable of selectively oxidising the sulphur atom of thioxanthone to thioxanthone sulphoxide without going further to produce the sulphone. Examples of suitable oxidising agents include cerium compounds, such as ceric ammonium nitrate, m-chloroperoxy benzoic acid and iodobenzene diacetate.

The reaction is normally and preferably effected in the presence of a solvent, the nature of which is not critical to the present invention, provided that it has no adverse effect on the reagents or on the reaction. Examples of suitable solvents include non-oxidisable solvents such as acetonitrile; and mixtures of any one or more of these organic solvents with water.

The temperature at which the reaction is carried out is likewise not critical to the present invention and may vary widely, depending on the reaction conditions and the nature of the reagents and solvent. We generally find it convenient to carry out the reaction at about ambient temperature, for example from 15 to 25° C. The time required for the reaction may also vary widely, depending mainly on the reaction temperature. However, under the preferred conditions outlined above, a period of from 1 to 10 hours will normally suffice.

When the reaction is complete, the desired product may be removed from the reaction mixture by conventional means, for example by washing the reaction mixture, e.g. with water, drying and then removing the solvent by evaporation under reduced pressure.

The resulting compound of formula (V) is then reacted with a compound of formula (VI):

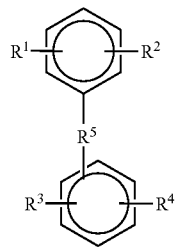

(VI)

(where $R^1$, $R^2$, $R^3$, $R^4$ and $R^5$ are as defined above), in the presence of an acid, to give a compound of formula (Ia):

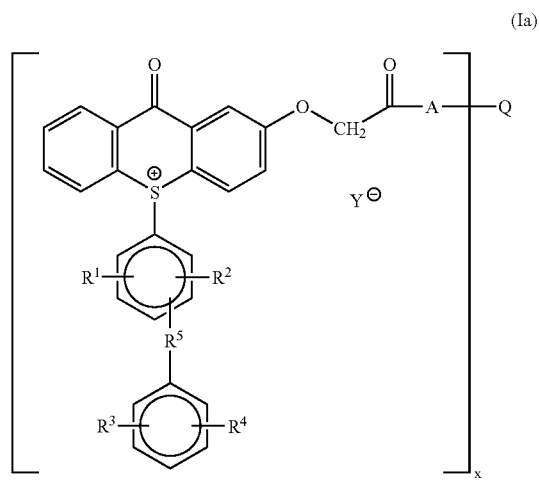

(Ia)

where $R^1$-$R^5$, A, Q and x are as defined above, and $Y^-$ represents an anion.

Where any one or more of $R^1$, $R^2$, $R^3$, or $R^4$ represents a hydroxy group, this is preferably protected, since it otherwise may react with the acid used in the reaction. The nature of the protecting group used is not critical to the invention, and any protecting group known in the art for use in compounds of this type may equally be used here. Examples of suitable protecting groups are described in "Protective Groups in Organic Synthesis" by T. W. Greene and P. G. M. Wuts, Second Edition, 1991, published by John Wiley & Sons, Inc.

The reaction is normally and preferably effected in a solvent, the nature of which is not critical, provided that it has no adverse effect on the reagents or on the reaction and provided that it can dissolve the reagents, at least to some extent. A suitable solvent is acetic acid.

The reaction is also preferably effected in the presence of a strong acid. Preferred is a combination of concentrated sulphuric acid and acetic anhydride.

A suitable reaction temperature is preferably below 15° C.

The anion $Y^-$ will be introduced by the reaction, and so, in general, the anion $Y^-$ will not be the anion $X^-$ which it is desired to incorporate in the final product. If so, then the desired anion may be introduced by an anion exchange reaction, as is well known in the field of synthetic chemistry.

Where a protected hydroxy group represented by $R^1$, $R^2$, $R^3$, or $R^4$ is present, the protecting group may, if desired, be removed by methods well known to those skilled in the art, as described in "Protective Groups in Organic Synthesis" above.

The compounds of the invention may then be separated from the reaction mixture by well known techniques and, if desired, further purified.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, and the cationic photoinitiator of the present invention, but may also include other components well known to those skilled in the art, for example, reactive diluents and, in the case of printing inks, a pigment.

A wide variety of monomers and prepolymers may be subjected to cationic photoinitiation using the compounds of the present invention as photoinitiators, and the nature of the monomers and prepolymers is not critical to the present invention. Such monomers and prepolymers typically contain cationically polymerisable groups, and general examples of such compounds include the epoxides, oxetanes, other cyclic ethers, vinyl compounds (such as vinyl and propenyl ethers, styrene and its derivatives and unsaturated polyesters), unsaturated hydrocarbons, lactones and, in the case of hybrid systems, acrylates and methacrylates.

Typical epoxides which may be used include the cycloaliphatic epoxides (such as those sold under the designations UVR6110 by Union Carbide or UVACURE 1500 by UCB), which are well known to those skilled in the art.

Other epoxy-functional oligomers/monomers which may be used include the glycidyl ethers of polyols [bisphenol A, alkyl diols or poly(alkylene oxides), which be di-, tri-, tetra or hexa-functional]. Also, epoxides derived by the epoxidation of unsaturated materials may also be used (e.g. epoxidised soybean oil, epoxidised polybutadiene or epoxidised alkenes). Naturally occurring epoxides may also be used, including the crop oil collected from *Vernonia galamensis*.

As well as epoxides, other reactive monomers/oligomers which may be used include the vinyl ethers of polyols [such as triethylene glycol divinyl ether, 1,4-cyclohexane dimethanol divinyl ether and the vinyl ethers of poly(alkylene oxides)]. Examples of vinyl ether functional prepolymers include the urethane-based products supplied by Allied Signal. Similarly, monomers/oligomers containing propenyl ether groups may be used in place of the corresponding compounds referred to above containing vinyl ether groups.

Similarly, compounds bearing oxetane groups may be used in place of the corresponding compounds referred to above containing epoxide groups. A typical oxetane is that derived from trimethylolpropane (3-ethyl-3-hydroxymethyloxetane).

Other reactive species can include styrene derivatives and cyclic esters (such as lactones and their derivatives).

It is also common to include polyols in ultraviolet cationic curable formulations, which promote the cross-linking by a chain-transfer process. Examples of polyols include the ethoxylated/propoxylated derivatives of, for example, trimethylolpropane, pentaerythritol, di-trimethylolpropane, di-pentaerythritol and sorbitan esters, as well as more conventional poly(ethylene oxide)s and poly(propylene oxide)s. Other polyols well known to those skilled in the art are the polycaprolactone diols, triols and tetraols, such as those supplied by Union Carbide.

Additives which may be used in conjunction with the principal components of the coating formulations of the present invention include stabilisers, plasticisers, pigments, waxes, slip aids, levelling aids, adhesion promoters, surfactants and fillers. Also, compounds which act as sensitisers for the photoinitiator, such as thioxanthone (and derivatives), benzophenone (and derivatives), hydroxyalkylphenones, anthracene (and derivatives), perylene, xanthone, pyrene and anthraquinone, may be included.

The compounds of the present invention may be included as photoinitiators in coating formulations such are well known in the art, and the precise composition of such formulations will vary depending upon the other components and the intended use, as is well known. However, a typical formulation for an ink coatable by flexography might be:

| | |
|---|---|
| Pigment | 8-20% |
| Photoinitiator | 2-6% |
| Monomer/prepolymer/oligomer | 30-90% |
| Polyol | 0-30% |
| Additives | 0-10% |

In order to enhance the solubility of the compounds of the present invention in the curable composition, they may first be dissolved in a suitable solvent, for example propylene carbonate.

The multi-functional initiators of formula (I) are especially suited for inks, especially printing inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference.

The invention is further illustrated by the following non-limiting Examples.

EXAMPLE 1

Preparation of Carboxymethoxythioxanthone

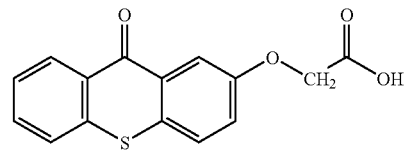

(II)

24 g sodium hydroxide was refluxed in 400 ml tetrahydrofuran for five minutes. 22.8 g (0.1 mols) hydroxythioxanthone was added and reflux continued for 1 hour, during which time the colour changed to bright red, indicating the formation of the sodium salt of hydroxythioxanthone. 35.1 g (0.21 mols) of ethyl bromoacetate was added and reflux was continued for three hours. After cooling to room temperature, 400 ml of deionised water were added with stirring, and the tetrahydrofuran was distilled out to yield a clear red solution. Reflux was continued for a further 2 hours in order to hydrolyse all the ester intermediate. The solution was then cooled to 50 C and 400 ml 1.0 M aqueous hydrochloric acid was added with stirring, causing the solid product to precipitate out. After refluxing for five minutes to be sure that all the sodium salt was converted to free acid, the solution was cooled to room temperature and stirred for two hours before filtering off the solid, washing with 400 ml deionised water and drying in a vacuum oven at 80 C.

Product yield 28.12 g (97%). Product analysed by NMR.

EXAMPLE 2

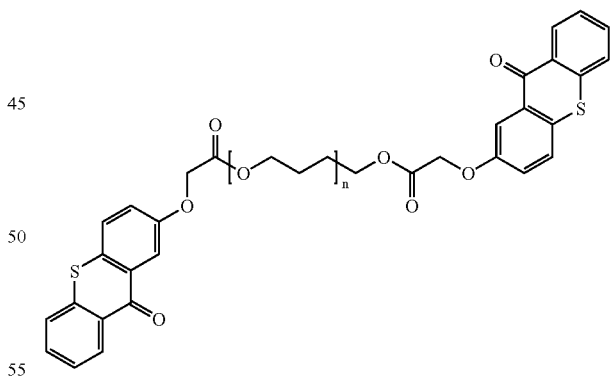

10 g (0.035 mols) carboxymethoxythioxanthone from Example 1 and 3.5 polytetrahydrofuran (250 molecular weight) were azeotropically refluxed in 75 ml toluene with 0.3 g p-toluenesulphonic acid monohydrate catalyst. After 15 hours, the solution was cooled and washed with 2×50 ml 0.1 M aqueous NaOH and 2×50 ml deionised water before drying over anhydrous magnesium sulphate. The solution was filtered and all solvent was removed on a rotary evaporator to yield a dark red high viscosity oil.

Product yield 9.05 g (81%). Product analysed by HPLC.

EXAMPLE 3

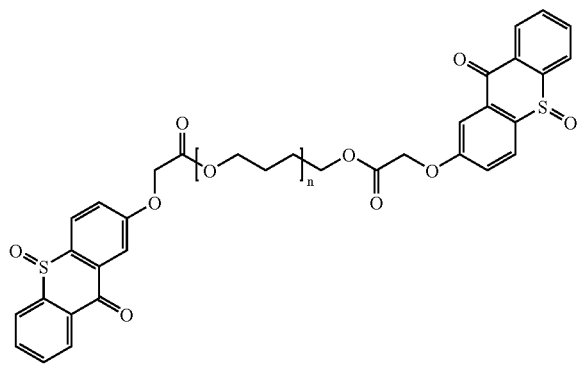

5.0 g of the product from Example 2 (0.0063 moles) was dissolved in 200 ml of a mixture of acetonitrile and water (75% acetonitrile, 25% water). Gentle heating was applied and 27.83 g ceric ammonium nitrate (0.051 moles) was added. The reaction mixture was stirred for 2 hours at room temperature and followed by thin layer chromatography (TLC). 130 ml of water was then added and the mixture was extracted with 200 ml of dichloromethane (DCM). Some insoluble material formed at the interface between the DCM and water. This was removed by filtration before separation was carried out. The dichloromethane layers were combined, dried with magnesium sulphate and then the solvent was removed on a rotary evaporator to yield the product.

Product yield 4.74 g (91%) of a pasty liquid. Product analysed by IR, HPLC and LC-MS.

EXAMPLE 4

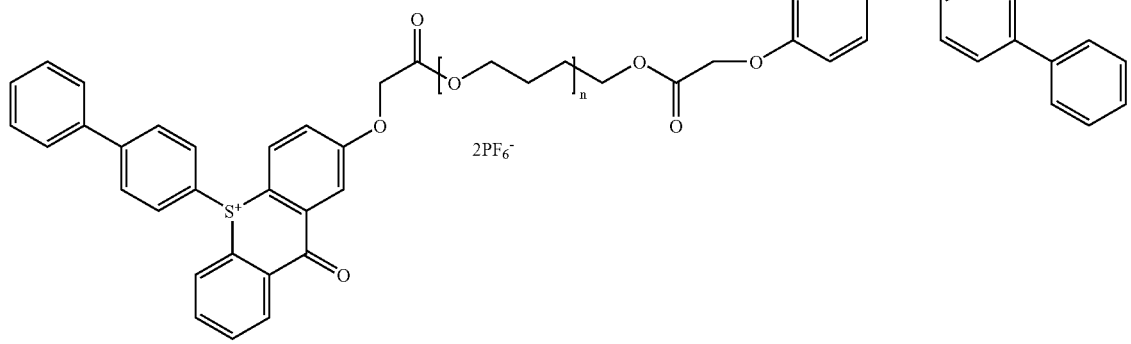

3.075 g of the product from Example 3 (0.00375 moles) and 1.604 g biphenyl (0.01040 moles), acetic acid (7 ml), dichloromethane (1.75 ml) and acetic anhydride (7 ml) were mixed in a round bottomed flask. The temperature of the mixture was reduced to <15° C. using a water/ice bath. Concentrated sulphuric acid (2.6 ml) was then added dropwise, making sure the temperature did not exceed 15° C. After addition was complete, the mixture was stirred for 2 hours, allowing the temperature to increase to room temperature. 100 ml of water was then added and the solution was extracted with 2×100 ml of dichloromethane. The dichloromethane was then removed on a rotary evaporator to yield 7.79 g of intermediate product. This was dissolved in a minimum of acetic acid and poured into a KPF6 solution (2.5 g in 75 ml water). This appeared to yield a viscous liquid which was extracted with dichloromethane and washed with 3×100 ml water.

Product yield 5.23 g (~100%) of a brown viscous liquid. Product analysed by IR, HPLC and LC-MS.

EXAMPLE 5

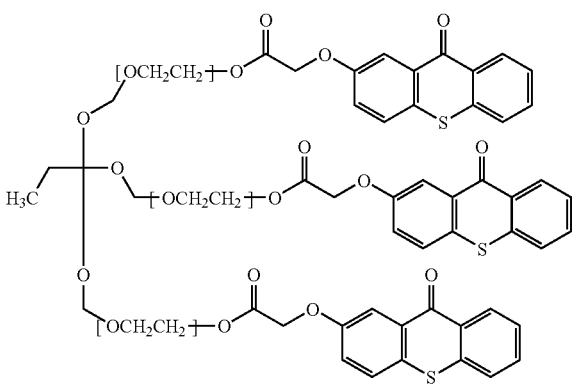

10 g (0.035 mols) carboxymethoxythioxanthone from Example 1 and 4.42 g (0.01 mols) ethoxylated trimethylolpropane (TP70 ex Perstorp) were azeotropically refluxed in 75 ml toluene with 0.3 g p-toluenesulphonic acid monohydrate catalyst. After 11 hours the solution was cooled and washed with 2×75 ml 0.5M aqueous $Na_2CO_3$ and 2×75 ml deionised water before drying over anhydrous magnesium sulphate. The solution was filtered and all solvent removed on a rotary evaporator to yield a dark red high viscosity oil.

Product yield 9.18 g (77%). Product analysed by HPLC and LC-MS.

EXAMPLE 6

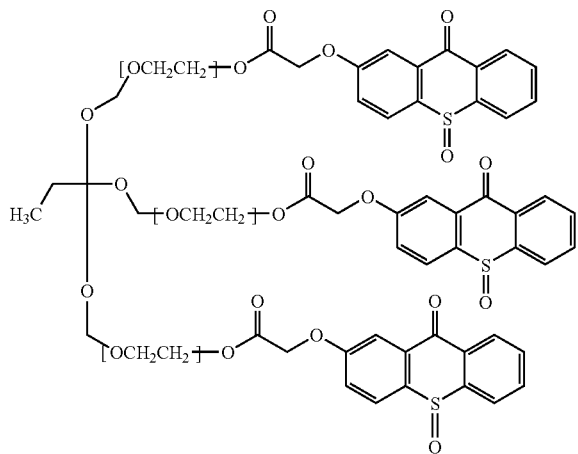

5.0 g of the product from Example 5 (0.00385 moles) was dissolved in 185 ml of a mixture of acetonitrile and water (75% acetonitrile, 25% water). Gentle heating was applied and 25.31 g ceric ammonium nitrate (0.046 moles) added. The reaction mixture was stirred for 2 hour at room temperature and followed by TLC. 120 ml of water was then added and the mixture was extracted with 200 ml of dichloromethane. Some insoluble material formed at the interface between the DCM and water. This was removed by filtration before separation was carried out. The dichloromethane layers were combined, dried with magnesium sulphate and then removed on a rotary evaporator to yield the product. This was purified by dissolving in a 1:1 mixture of dichloromethane & acetonitrile and washing with 3×100 ml of water before drying over magnesium sulphate and removing all solvent on a rotary evaporator.

Product yield 3.75 g (68.9%) of a pasty liquid. Product analysed by IR, HPLC and LC-MS.

EXAMPLE 7

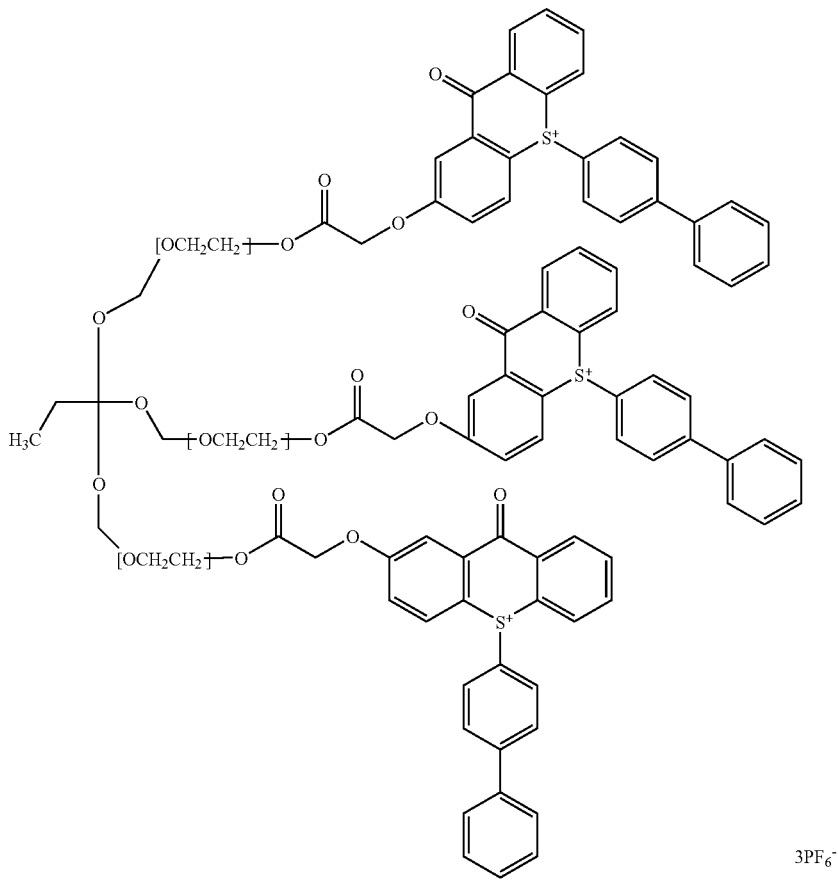

2.5 g of the product from Example 6 (0.00185 moles) and 1.19 g biphenyl (0.0075 moles), acetic acid (5.2 ml), dichloromethane (1.3 ml) and acetic anhydride (5.2 ml) were mixed in a round bottomed flask. The temperature of the mixture was reduced to <15° C. using a water/ice bath. Concentrated sulphuric acid (1.9 ml) was then added dropwise, making sure the temperature did not exceed 15° C. After addition was complete, the mixture was stirred for 2 hours, allowing the temperature to increase to room temperature. 100 ml of water was then added and the solution was extracted with 2×100 ml of dichloromethane. The dichloromethane was then removed on a rotary evaporator to yield 6.5 g of intermediate product. This was dissolved in a minimum of acetic acid and poured into a KPF6 solution (2 g in 65 ml water). This appeared to yield a viscous liquid which was extracted with dichloromethane and washed with 2×100 ml water.

Product yield 3.05 g (74.96%) of a brown high viscosity liquid. Product analysed by IR, HPLC and LC-MS.

EXAMPLE 8

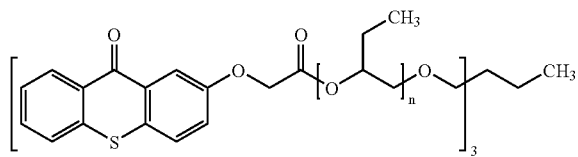

42.9 g (0.15 mols) carboxymethoxythioxanthone from Example 1 and 25.52 g (0.04 mols) of butoxylated trimethylolpropane (Simulsol TOMB ex Seppic) were azeotropically refluxed under nitrogen in 300 ml toluene with 0.3 g p-toluenesulphonic acid monohydrate catalyst and 0.1 g butylated hydroxytoluene. After 13 hours, the solution was cooled to 35° C. and washed with 250 ml 10% aqueous potassium carbonate solution and 250 ml deionised water before drying by azeotropic distillation. The solution was filtered and all solvent was removed on a rotary evaporator to yield an orange high viscosity oil.

Product yield 38.5 g (67.0%). Product analysed by HPLC and IR.

EXAMPLE 9

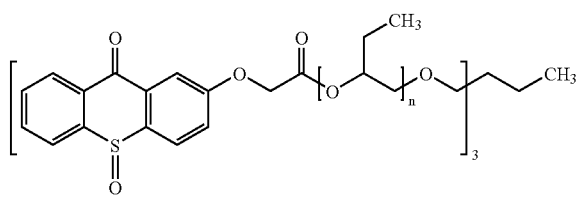

20 g of the product from Example 8 (0.0139 mols) was dissolved in 600 ml acetonitrile at 60° C. The solution was cooled to 25° C. and 200 ml deionised water added, causing the formation of a fine emulsion. 90.9 g of ceric ammonium nitrate (0.1668 mols) was added and the mixture stirred at room temperature for 2.5 hours. The solution was poured into 500 ml deionised water and the product extracted into 700 ml dichloromethane. The dichloromethane layer was washed with 300 ml and 500 ml deionised water, dried over anhydrous magnesium sulphate and then all the solvent removed on a rotary evaporator.

Product yield 17.0 g (82.1%) of an orange oil. Product analysed by HPLC and IR.

EXAMPLE 10

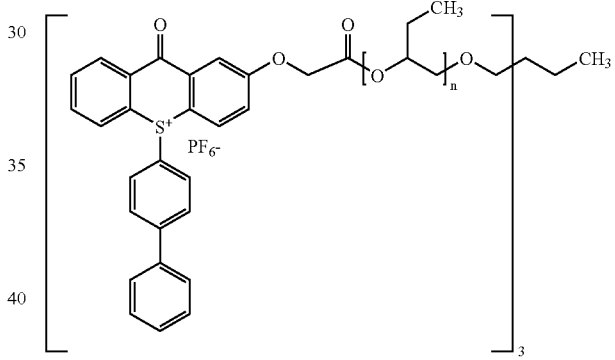

3.2 g of the product from Example 9 (0.00215 mols) and 0.66 g biphenyl (0.0043 mols) were dissolved in 15 ml acetic anhydride in a round bottomed flask. The temperature of the mixture was reduced to 5° C. using a water/ice bath. Concentrated sulphuric acid (3.15 g) was then added dropwise, making sure the temperature did not exceed 20° C. After addition was complete, the mixture was stirred for 10-15 minutes, allowing the temperature to increase to room temperature, and then added to a solution of 1.385 g KPF6 (0.0075 mols) in 13 ml methanol and 15 ml deionised water. The solution was stirred at ambient temperature for ~45 minutes before extracting the product into 50 ml dichloromethane. The dichloromethane solution was washed with 3*50 ml deionised water, dried over anhydrous magnesium sulphate and all solvent removed on a rotary evaporator.

Product yield 2.87 g (57.2%) of a brown high viscosity oil. Product analysed by HPLC and IR.

EXAMPLE 11

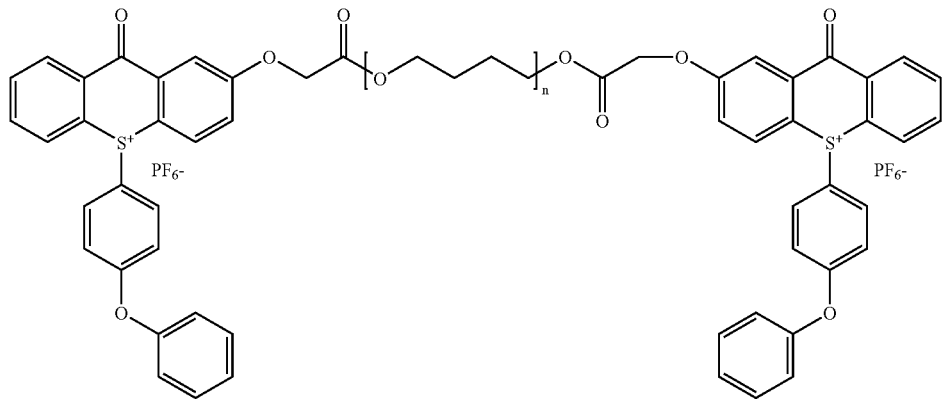

6.2 g of the product from Example 3 (0.0075 mols) and 2.55 g of diphenyl ether (0.015 mols) were dissolved in 30 ml acetic anhydride in a round bottomed flask. The temperature of the mixture was reduced to 5° C. using a water/ice bath. Concentrated sulphuric acid (6.3 g) was then added dropwise, making sure the temperature did not exceed 20° C. After addition was complete, the mixture was stirred for 10-15 minutes, allowing the temperature to increase to room temperature, and then added to a solution of 3.04 g KPF6 (0.0165 mols) in 26 ml methanol and 30 ml deionised water. The solution was stirred at ambient temperature for ~45 minutes before extracting the product into 100 ml dichloromethane. The dichloromethane solution was washed with 3*100 ml deionised water, dried over anhydrous magnesium sulphate and all solvent removed on a rotary evaporator.

Product yield 8.75 g (82.2%) of a high viscosity orange oil. Product analysed by HPLC and IR.

EXAMPLE 12

6.2 g of the product from Example 3 (0.0075 mols) and 2.31 g of biphenyl (0.015 mols) were dissolved in 30 ml acetic anhydride in a round bottomed flask. The temperature of the mixture was reduced to 5° C. using a water/ice bath. Concentrated sulphuric acid (6.3 g) was then added dropwise, making sure the temperature did not exceed 20° C. After addition was complete, the mixture was stirred for 10-15 minutes, allowing the temperature to increase to room temperature, and then added to a solution of 4.74 g KSbF6 (0.0165 mols) in 26 ml methanol and 30 ml deionised water. The solution was stirred at ambient temperature for ~45 minutes before extracting the product into 100 ml dichloromethane. The dichloromethane solution was washed with 3*100 ml deionised water, dried over anhydrous magnesium sulphate and all solvent removed on a rotary evaporator.

Product yield 9.3 g (78.9%) of a high viscosity brown oil. Product analysed by HPLC and IR.

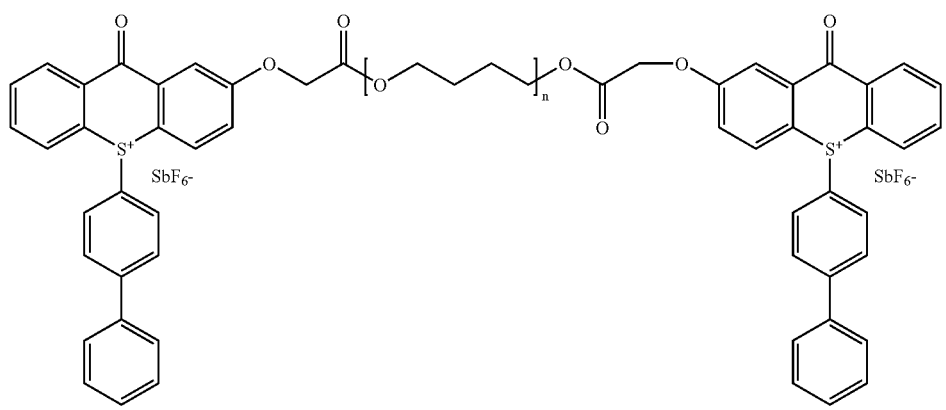

EXAMPLE 13

Varnish Formulations

The following varnish formulations were used in the evaluation experiments.

| Material Code/ Description | Standard Varnish | Experimental Varnish |
|---|---|---|
| Uvacure 1500 | 91.8 | 91.8 |
| Tegorad 2100 | 0.2 | 0.2 |
| Propylene carbonate | 4.0 | 4.0 |
| Standard Photoinitiator | 4.0 | — |
| Experimental Photoinitiator | — | 4.0 |

The standard photoinitiators used were Uvacure 1592 (triarylsulphonium salt photoinitiator from UCB, supplied as a 50% solution in propylene carbonate) and Irgacure 250 (diaryliodonium salt photoinitiator from CIBA Speciality Chemicals, supplied as a 75% solution in propylene carbonate).

Uvacure 1500 is a cycloaliphatic epoxide monomer from UCB

Tegorad 2100 is a wetting aid from TEGO

Summary of Curing Experiments.

The varnishes were printed onto Leneta opacity charts using a No.0 K-bar and draw down pad. The prints were passed through a Primarc Maxicure UV curing rig fitted with a medium pressure mercury arc lamp at line speeds of 80 and 100 m/min. The UV lamp power is rated at 300 Watts/inch but was used on it's half power setting to aid differentiation of performance. The number of passes to achieve complete cure was determined using the "thumb-twist" test.

| Photoinitiator | No. passes to cure at 80 m/min | No. passes to cure at 100 m/min | Odour | Colour of cured film |
|---|---|---|---|---|
| Uvacure 1592 | 1 | — | Strong, diphenyl sulphide | Colourless |
| Irgacure 250 | 3 | — | Very strong | Colourless |
| Example 4 | 1 | 1 | Low | Slightly yellow |
| Example 7 | 1 | 1 | Low | Slightly yellow |
| Example 10 | 1 | 1 | Low | Slightly yellow |
| Example 11 | 1 | 1 | Slight | Slightly yellow |
| Example 12 | 1-2 | 2 | Low | Slightly yellow |

These results demonstrate that with the exception of Example 12, all the experimental photoinitiators have cure speed equivalent to the standard photoinitiator Uvacure 1592 and that all are superior to the standard photoinitiator Irgacure 250. All the experimental photoinitiators have superior odour compared to both standard photoinitiators. The slight yellow colouration of the cured films can be significantly reduced by the use of lower photoinitiator levels and other formulating options known to those skilled in the art.

EXAMPLE 14

Magenta Ink Formulations

The following magenta ink formulations were used in the evaluation experiments.

| Material Code/ Description. | Standard Ink | Experimental Ink |
|---|---|---|
| Pigment concentrate | 56.8 | 56.8 |
| Uvacure 1500 | 34.7 | 34.7 |
| Tegorad 2100 | 0.5 | 0.5 |
| Propylene carbonate | 4.0 | 4.0 |
| Standard Photoinitiator | 4.0 | — |
| Experimental Photoinitiator | — | 4.0 |

The standard photoinitiators used were Uvacure 1592 (triarylsulphonium salt photoinitiator from UCB, supplied as a 50% solution in propylene carbonate) and Irgacure 250 (diaryliodonium salt photoinitiator from CIBA Speciality Chemicals, supplied as a 75% solution in propylene carbonate).

Uvacure 1500 is a cycloaliphatic epoxide monomer from UCB.

Tegorad 2100 is a wetting aid from TEGO.

Summary of Curing Experiments.

The inks were printed onto a white OPP substrate (Propafilm RB30 ex UCB) using an "Easiproof" hand held flexo proofer with anilox tool 41. The prints were passed through a Primarc Maxicure UV curing rig fitted with a 300 Watts/inch medium pressure mercury arc lamp at several different line speeds and lamp power settings. The number of passes to achieve complete cure was determined using the "thumb-twist" test.

| | Lamp at 50% power | | Lamp at 100% Power |
|---|---|---|---|
| Photoinitiator | No. passes to cure at 80 m/min | No. passes to cure at 100 m/min | No. passes to cure at 120 m/min |
| Uvacure 1592 | 1 | 2 | 2 |
| Irgacure 250 | — | 4 | 2 |
| Example 4 | 2 | 2 | 2 |
| Example 11 | 3 | 4 | 2-3 |
| Example 12 | 4 | 4-5 | 3 |

These results demonstrate that the novel photoinitiators of this invention have similar cure performance in inks to standard commercial cationic photoinitiators. In particular, Example 4 is very reactive and gives cure performance almost equivalent to the best commercial standard photoinitiator Uvacure 1592.

EXAMPLE 15

GC-MS Headspace Analysis

The following varnish formulations were used in the evaluation experiments.

| Material Code/ Description | Sulphonium salt formulations | Iodonium salt formulation |
|---|---|---|
| Uvacure 1500 | 75 | 77.5 |
| TMPO | 20.9 | 18.9 |
| Tegorad 2100 | 0.1 | 0.1 |

-continued

| Material Code/ Description | Sulphonium salt formulations | Iodonium salt formulation |
|---|---|---|
| Propylene carbonate | 2 | — |
| Photoinitiator | 2 | 1.5 |
| Esacure KIP 150 | — | 2 |

The standard photoinitiators used were Uvacure 1592 (triarylsulphonium photoinitiator from UCB, supplied at 50% in propylene carbonate) and IGM 440 (diaryliodonium photoinitiator from IGM.

Uvacure 1500 is a cycloaliphatic epoxide monomer from UCB.

Tegorad 2100 is a wetting aid from TEGO.

TMPO is a monofunctional oxetane alcohol diluent from Perstorp.

Esacure KIP 150 is a hydroxyalkylphenone photoinitator from Lamberti.

The varnishes were printed onto aluminium foil using a No.0 K-bar and draw down pad. The prints were passed twice through a Primarc Maxicure UV curing rig fitted with a 300 Watts/inch medium pressure mercury arc lamp at 80 m/min. Under these conditions the samples were over-cured, which was desirable in order to maximise the amount of by-product formation. 200 cm² of each sample was placed in a sealed tube and subjected to a standard headspace analysis procedure where they are heated to 200° C. for 10 minutes and then the headspace volume transferred to a gas chromatograph fitted with a mass spectrometer detector via a heated transfer line.

The compounds detected in these analyses are shown below. No attempt was made to quantify individual materials. Note that there were also several peaks common to all samples which derive from the Uvacure 1500.

| Photoinitiator | Materials detected in Head-space procedure |
|---|---|
| Uvacure 1592 | Diphenyl sulphide |
| | Several small unidentified peaks* |
| IGM 440 | Toluene |
| | Iodobenzene |
| | Several unidentified peaks |
| Example 4 | Biphenyl |

*Benzene would also be expected from this analysis but was not seen due to the solvent delay used in this standard GC method.

These results demonstrate that for Example 4, the only photoinitiator by-product detected is biphenyl, which is of limited toxicological concern for food packaging inks as it is itself an approved food additive material. This is in contrast with the undesirable materials released from the 2 standard photoinitiators.

The invention claimed is:

1. Photoinitiator compounds of formula (I):

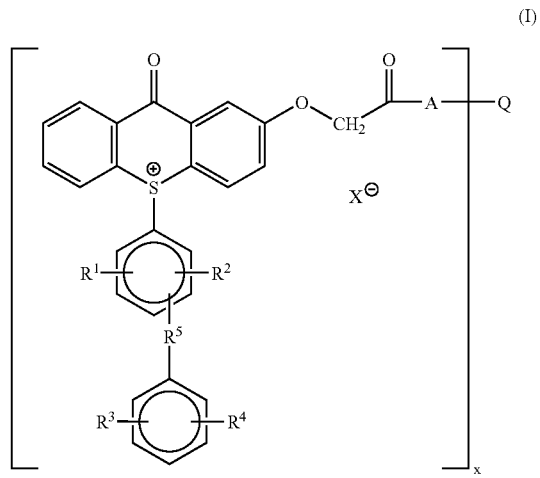

where:
A represents a direct bond or a group of formula —[O(CHR$^7$CHR$^6$)$_a$]$_y$—, —[O(CH$_2$)$_b$CO]$_y$—, or —[O(CH$_2$)$_b$CO]$_{y-1}$)—[O(CHR$^7$CHR$^6$)$_a$]—, where:
R$^6$ and R$^7$ are independently selected from hydrogen atoms and methyl groups, provided that both R$^6$ and R$^7$ do not represent methyl groups;
a is a number from 1 to 2;
b is a number from 4 to 5;
Q is a residue of a polyol having from 2 to 6 hydroxy groups;
x is a number greater than 1 but no greater than the number of available hydroxyl groups in Q;
when x is a number greater than 1 but no greater than 2, y is a number from 1 to 10; or when x is a number greater than 2, y is a number from 3 to 10; R$^1$, R$^2$, R$^3$ and R$^4$ are independently selected from hydrogen atoms, hydroxy groups, and C$_1$-C$_4$ alkyl groups;
or R$^1$ and R$^3$ are joined to form a fused ring system with the benzene rings to which they are attached; and
R$^5$ represents a direct bond, an oxygen atom or a —CH$_2$— group.

2. Compounds according to claim 1, in which y is a number from 3 to 10.

3. Compounds according to claim 1, in which A represents a group of formula —[O(CHR$^7$CHR$^6$)$_a$]$_y$— where a is an integer from 1 to 2, and y is a number from 1 to 10.

4. Compounds according to claim 1, in which A represents a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is a number from 3 to 10.

5. Compounds according to claim 1, in which A represents a group of formula —[O(CH$_2$)$_b$CO]$_y$—, where b is a number from 4 to 5 and y is a number from 3 to 10.

6. Compounds according to claim 1, in which A represents a group of formula —[O(CH$_2$)$_b$CO]$_{y-1}$—[O(CHR$^7$CHR$^6$)$_a$]—, where a is a number from 1 to 2, b is a number from 4 to 5 and y is a number from 3 to 10.

7. Compounds according to claims 1, in which y is a number from 3 to 6.

8. Compounds according to claim 1, in which residue of formula Q-(A-)$_x$ in said compound of formula (I) has a molecular weight no greater than 2000.

9. Compounds according to claim 8, in which the residue Q-(A-)$_x$ has a molecular weight no greater than 1200.

10. Compounds according to claim 9, in which the residue Q-(A-)$_x$ has a molecular weight no greater than 1000.

11. Compounds according to claim 10, in which the residue Q-(A-)$_x$ has a molecular weight no greater than 800.

12. Compounds according to claim 1, in which Q is a residue of ethylene glycol, propylene glycol, butylene glycol, hexanediol, decanediol, glycerol, trimethylolpropane, di-trimethylolpropane, pentaerythritol or di-pentaerythritol.

13. Compounds according to claim 1, in which A is a direct bond.

14. Compounds according to claim 1, in which two, three or four of $R^1$, $R^2$, $R^3$ and $R^4$ represent hydrogen atoms.

15. Compounds according to claim 14, in which all of $R^1$, $R^2$, $R^3$ and $R^4$ represent hydrogen atoms.

16. Compounds according to claim 1, in which $R^5$ is a direct bond.

17. An energy curable composition, comprising: (a) a polymerisable monomer, prepolymer or oligomer; and (b) a photoinitiator according to claim 1.

18. A printing ink containing an energy curable composition according to claim 17.

19. A process for preparing a cured polymeric composition by exposing a composition according to claim 17.

20. A process according to claim 19, in which the radiation is ultraviolet.

21. A process for preparing a cared polymeric composition by exposing a printing ink according to claim 18 to radiation.

22. A process according to claim 21, in which the radiation is ultraviolet.

* * * * *